US00PP10799P

United States Patent [19]

Ninomiya

[11] Patent Number: Plant 10,799

[45] Date of Patent: Feb. 23, 1999

[54] HYBRID TEA ROSE PLANT NAMED 'TANPINAISO'

[75] Inventor: Flora Ninomiya, Richmond, Calif.

[73] Assignee: Bear Creek Gardens, Inc., Medford, Oreg.

[21] Appl. No.: 838,421

[22] Filed: Apr. 7, 1997

[51] Int. Cl.[6] ..... A01H 5/00

[52] U.S. Cl. ..... Plt./18

[58] Field of Search ..... Plt./18, 11

[56] References Cited

U.S. PATENT DOCUMENTS

P.P. 7,660 10/1991 Evers ..... Plt./18

OTHER PUBLICATIONS

UPOU–ROM, 1997/06, Plant Variety Database, GTI Jouve Retrieval Software, citation for 'Tanpinaiso'.

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the hybrid tea class, having light pink, long-lasting high centered blooms with slightly darker centers on strong, long stems with very few thorns and medium green, large, long leaves.

1 Drawing Sheet

The present invention relates to a new and distinct variety of rose plant of the hybrid tea class which was originated by me by discovering in a nursery in Richmond, Calif. a spontaneous flower color mutation on one branch of a plant of the variety Osiana, U.S. Plant Pat. No. 7,660.

The rose plant TANpinaiso differs from Osiana, its parent, only in its flower color. The two plants are alike in flower size, anthers, pollen, leaves, stems, thorns and in growth habit.

Asexual reproduction by me of this new variety by budding, as performed at Richmond, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Parent.*—Mutant of Osiana (U.S. Plant Pat. No. 7660).

Classification:

*Botanical.*—Rosa hybrida.

*Commercial.*—Hybrid tea.

Flower

Observations made from specimens grown in a greenhouse environment at Somis, Calif. from March 1996 to January 1997.

Blooming habit: Recurrent.

Bud:

*Size.*—2 to 2-½ inches long when the petals start to unfurl.

*Form.*—The bud form is long, pointed ovoid.

*Color.*—When sepals first divide, bud color is Red Group 49D. When half blown, the upper sides of the petals are Red Group 49B in the center of the flower, fading to Red Group 49C and then Red Group 49D at the edge of the flower; and the lower sides of the petals are Red Group 49B.

*Sepals.*—Color: Green Group 138B. Surface texture: Covered in fine hairs. There are three normally appendaged sepals. There are two unappendaged sepals with hairy edges.

*Receptacle.*—Color: Green Group 137D. Shape: Funnel. Size: Large (½×½ inch). Surface: Smooth.

*Peduncle.*—Length: Medium (3 inches). Surface: Smooth, and some glands. Color: Medium green. Strength: Stiff, erect, heavy.

Bloom:

*Size.*—Very large. Average open size is 5 to 6 inches.

*Borne.*—Singly.

*Stem.*—Very long, strong. Average length is greater than 26 inches.

*Form.*—When first open: High centered. Permanence: Retains its from to the end. Outer petals curl back, quill fashion.

*Petalage.*—Number of petals under normal conditions: 30 to 35.

*Color.*—The upper sides of the petals are Red Group 49B in the center of the flower, fading to Red Group 49C and Red Group 49D at the flower edges. The reverse sides of the petals are Red Group 49B. The base of the petals each has a small (¼×¼ inch), yellowish half-moon at the point of attachment. The major color on the upper side is Red Group 49B.

*Variegations.*—None.

*Discoloration.*—The general tonality at the end of the first day: No change. At the end of the third day: As the flower opens, the pink color fades on the flower edges but never fades beyond Red Group 49D.

*Fragrance.*—Moderate.

Petals:

*Texture.*—Thick.

*Shape.*—Round.

*Form.*—Tips slightly recurved; edges slightly quilled.

*Arrangement.*—Imbricated, with no petaloids in the center.

*Persistence.*—Drop off cleanly.

*Lastingness.*—On the plant: Long (7 days). As a cut flower: Long (7–10 days).

Reproductive Parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Very light pink.

*Stigmas.*—Color: Yellow.

Form: Bush.

Growth: Very vigorous; upright; branching. After one year without pruning plant will be 7-feet tall and 4-feet wide.

Foliage: Number of leaflets on normal mid-stem leaves: 5, occasionally 7.

*Size.*—Large (6×4-½ inches).

*Quantity.*—Normal.

*Color.*—New foliage: Greyed-Red Group 178A (upper and lower surface). Old foliage: Upper surface is Green Group 137A; lower surface is Green Group 138A.

Leaflets:

*Shape.*—Broadly oval to oval.

*Texture.*—Upper side: Leathery.

*Edge.*—Serrated.

*Serration.*—Single, small.

*Petiole rachis.*—Color: Reddish, Red-Purple Group 59A at the leaflet nodes.

*Petiole underside.*—Smooth, with occasional prickles.

*Stipules.*—Medium, bearded (½ inch to ¾ inch).

*Disease resistance.*—Resistant to mildew under normal growing conditions at Richmond, Calif.

Wood:

*New wood.*—Color: Close to Greyed-Red 178A. Bark: Smooth.

*Old wood.*—Color: Green Group 138A. Bark: Smooth.

Prickles:

*Quantity.*—On main canes from base: Few. On laterals from main canes: Ordinary.

*Form.*—Medium (¼ inch), hooked downward.

*Color when young.*—Red-Purple Group 183A.

*Color when old.*—Greyed-Orange Group 176D.

Small Prickles:

*Quantity.*—On main stalks: None. On laterals: Few.

I claim:

1. A new and distinct variety of rose plant of the hybrid tea class, substantially as herein shown and described, characterized particularly as to novelty by the unique combination of its light pink, long-lasting high centered blooms with slightly darker centers on strong, long stems with very few thorns and medium green, large, long leaves.

* * * * *

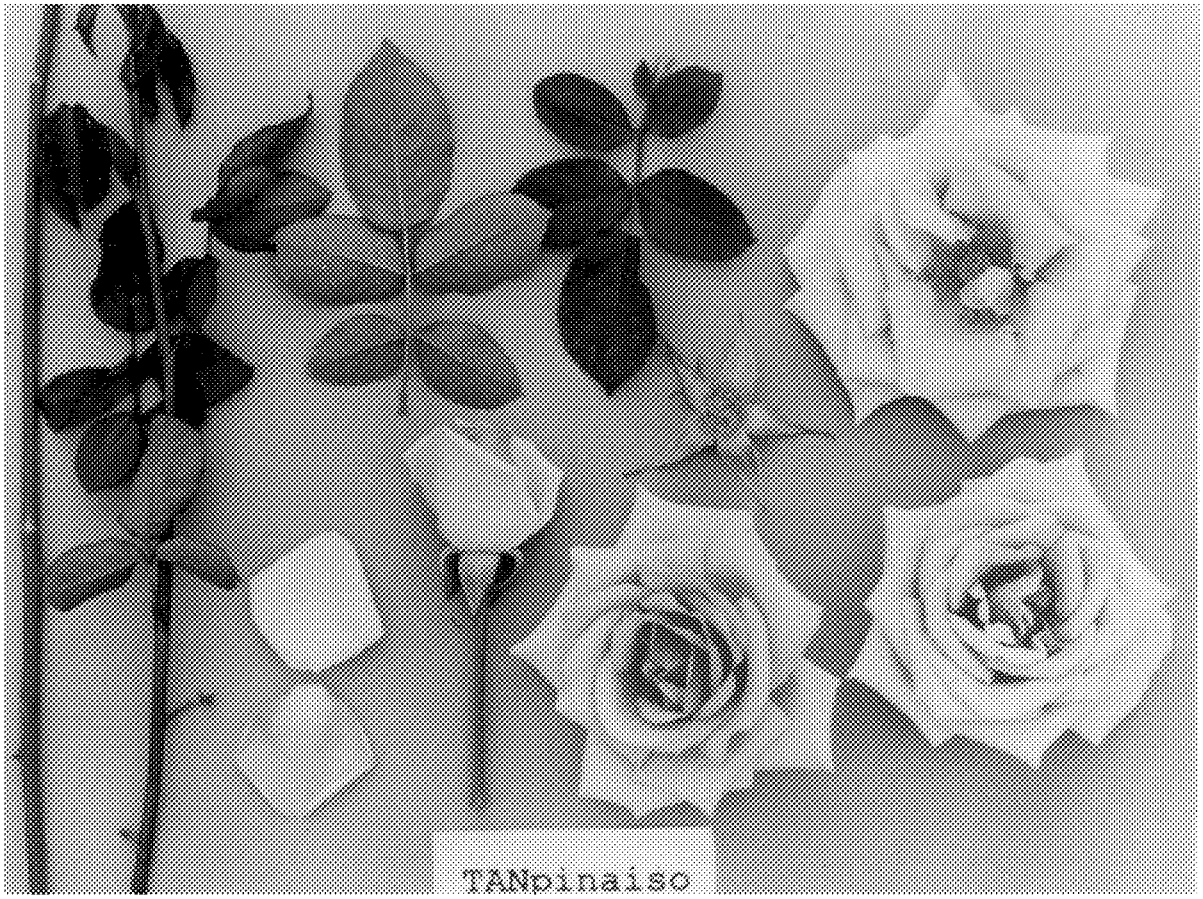
TANpinaiso